United States Patent [19]

Warner

[11] 4,025,643
[45] May 24, 1977

[54] RODENT REPELLENT POWDERS AND PREPARATION THEREOF

[75] Inventor: Paul F. Warner, Phillips, Tex.

[73] Assignee: Phillips Petroleum Company, Bartlesville, Okla.

[22] Filed: Jan. 23, 1975

[21] Appl. No.: 543,638

[52] U.S. Cl. ............................. 424/300; 424/184
[51] Int. Cl.² .................. A01N 9/12; A01N 9/20
[58] Field of Search .................... 424/30, 300, 84

[56] References Cited

UNITED STATES PATENTS

| | | | |
|---|---|---|---|
| 2,862,850 | 12/1958 | Goodhue | 424/300 |
| 3,643,450 | 2/1972 | Stansbury et al. | 424/30 |
| 3,740,201 | 6/1973 | Woodruff | 424/30 |
| 3,879,539 | 4/1975 | Enders | 424/324 |

OTHER PUBLICATIONS

Chemical Abstracts, vol. 77 (1972), p. 30350w.

*Primary Examiner*—V. D. Turner

[57] ABSTRACT

Free-flowing rodent repellent powders are provided in which a rodent repellent effective N,N-dialkyl-sulfenyl dithiocarbamate is admixed with a chemically inert grinding aid having a density of 5 pounds per cubic foot or less to form a non-caking composition. A solids suspending agent, inert to the N,N-dialkyl-sulfenyl dithiocarbamate, and a wetting agent are admixed with the rodent repellent and the grinding agent to produce a water-dispersible, free-flowing powder. The composition is an effective rodent repellent as a dry powder of two components, as a dispersible powder of four components, or as an aqueous disperson. A method is provided for preparing the free-flowing powder which entails grinding crystals of the N,N-dialkyl-sulfenyl dithiocarbamate with the low-density grinding aid or in combination with the solids suspending agent and the wetting agent for up to about 15 minutes.

9 Claims, No Drawings

RODENT REPELLENT POWDERS AND PREPARATION THEREOF

BACKGROUND OF THE INVENTION

This invention is related to rodent repelling compositions and the preparation of rodent repelling compositions. In one of its aspects this invention is related to rodent repellent compositions that are free-flowing powders. In another of its aspects this invention is related to free-flowing, rodent repellent powders that are readily dispersible in water. In yet another of its aspects this invention is related to dispersions of rodent repellent powders in water. In another of its aspects this invention relates to a method for preparing free-flowing, rodent repellent powder compositions; free-flowing, rodent repellent powder compositions that are dispersible in water; and free-flowing, rodent repellent compositions that are dispersed in water. In yet another of its aspects this invention relates to rodent repellent compositions that are prepared by specified methods for preparing free-flowing powders; dispersible, free-flowing powders; and dispersions.

This invention is particularly concerned with rodent repellent compositions based on a rodent repellent effective N,N-dialkyl-sulfenyl dithiocarbamate such as are set forth in U.S. Pat. No. 2,862,850. The rodent repellent N,N-dialkyl-sulfenyl dithiocarbamates, particularly N,N-dimethyl-S-tert-butylsulfenyl dithiocarbamate, set forth in that patent have been effectively introduced into commerce as crystals of the pure compounds or as solutions in xylene. Numerous problems resulted from the shipping and storage of the rodent repellent compounds in these forms.

In the crystalline form, the crystals or flakes have a tendency to lump together in a few weeks unless the crystals are purified above 96 mole percent. In solution in xylene, storage cannot be effected in carbon steel drums because the solution will blacken within a few days. Phenolic coated drums or stainless steel or aluminum drums are necessary for storage of the xylene solution. The solubility of the rodent repellent in xylene is sufficiently limited that crystallization occurs at about 32° F. so that the solution must be kept in a heated warehouse during the winter months and outdoor application using the solutions is limited during cold weather.

It has now been found that effective rodent repellent, free-flowing powders and free-flowing powders that are readily dispersible in water can be prepared using an N,N-dialkyl-sulfenyl dithiocarbamate as the base rodent repellent. Other aspects as well as the several advantages of this invention will be apparent to those skilled in the art upon reading the specification and the appended claims.

SUMMARY OF THE INVENTION

By the process of this invention a rodent repellent, free-flowing powder composition is provided which is composed of an N,N-dialkyl-sulfenyl dithiocarbamate effective as a rodent repellent admixed with a chemically inert grinding aid having a density of up to about 5 pounds per cubic foot. The grinding aid is admixed with the rodent repellent in an amount sufficient to provide non-caking characteristics to the composition. This two-component rodent repellent powder is effective when used as a dust. When the grinding agent is chosen from certain low-density silica grinding aids the powder can be effectively dispersed in water for use as a spray.

A free-flowing, rodent repellent wettable powder is also provided which is composed of a solids suspending agent and a wetting agent, both chemically inert to the N,N-dialkyl-sulfenyl dithiocarbamate, admixed with the grinding aid and N,N-dialkyl-sulfenyl dithiocarbamate. This composition provides the additional versatility of being generally useful both as a free-flowing powder and being readily dispersible in an aqueous dispersion for spraying application.

A method is also provided for producing both the two-component free-flowing powder and the four-component dispersible, wettable powder.

Characteristics of N,N-dialkly-sulfenyl dithiocarbamate useful in the compositions of this invention require, for best results, in producing a free-flowing powder that the grinding agent and the crystals of the dithiocarbamate be ground together to form an admixture and that the grinding not exceed a period of time of about 15 minutes. It has been found that grinding of the components for more than about 15 minutes either with or without the addition of solid suspending agents and wetting agents results in sticking of the admixture to the grinding apparatus with resulting loss of material and poorer flow characteristics for the compositions. The method of preparation for these compositions is, therefore, particularly important. The compositions of this invention can be seen, therefore, to be most effective as the product of the process set forth herein.

DESCRIPTION OF THE PREFERRED EMBODIMENT

The rodent repellent compounds useful as the essential active ingredient in the compositions of this invention are N,N-dialkyl-sulfenyl dithiocarbamates as set forth in U.S. Pat. No. 2,862,850. More specifically, N,N-dimethyl-S-methylsulfenyl dithiocarbamate is preferred. The rodent repellent compounds useful in this invention can be prepared by any convenient method. One method comprises reacting an alkali metal salt of N-substituted dithiocarbamate with an aliphatic sulfenyl thiocyanate. Further details regarding this method of preparing said compounds can be found in U.S. Pat. No. 2,390,713. Another method for the preparation of the rodent repellent compounds comprises reacting a lower alkyl sulfenyl halide with salts of N-substituted dithiocarbamate acid in aqueous solution as disclosed in U.S. Pat. No. 2,792,394. The latter method of preparation is a presently preferred method.

Specific compounds useful as rodent repellents in the present invention are N,N-dimethyl-S-methylsulfenyl dithiocarbamate and N,N-dimethyl-S-tert butylsulfenyl dithiocarbamate. The more preferred compound is N,N-dimethyl-S-tert butylsulfenyl dithiocarbamate. The rodent repellent is used in concentrations of 11–95 weight percent of the total mixture in combination with a low-density grinding aid as the only other component of the mixture with a preferred range of 85–89 weight percent of the total mixture as rodent repellent. When the rodent repellent is used in conjunction with a suspending agent and wetting agent along with the grinding aid it makes up 10–90 weight percent of the total mixture or is used in the preferred amount of 68–72 weight percent of the mixture of the four components.

The rodent repellent is used with a sufficient amount of a low-density inert material to allow the grinding of crystals of the rodent repellent into a powder with minimal fouling of a grinding apparatus such as a ball mill. The low-density inert material is, therefore, referred to in this application as a grinding aid. It has been found that low-density clays and silicas having a density of 5 pounds per cubic foot or less are particularly suitable for use in this invention. Some of the grinding aids useful in this invention are bentonite clay, attapulgite clay, and low-density silicas such as Cab—O—Sil EH-5, a product of the Cabot Corporation, and Syloid Silica 244, a product of the W. R. Grace & Company. Of these materials Cab—O—Sil EH-5, having a density of about 2.3 pounds per cubic foot, is the presently preferred grinding aid. The use of grinding aids in a two-component mixture with the rodent repellent has been found to produce an effective, free-flowing powder when the grinding aid comprises about 5 to about 89 percent of the total mixture, with a preferred range of about 11 to about 15 percent of the two-component mixture comprising grinding aid. In the four-component mixture in which a suspending agent and a wetting agent are also present the grinding aid can be present effectively in the range of about 5 to about 80 percent by weight of the total mixture and, preferably, is present in the range of about 9 to about 12 percent by weight of the total mixture. It has been found that on a weight basis at least three times as much of the clay material is required to keep the grinding mill clean while grinding as is necessary when using the silicas.

As has been noted above, the two-component mixture of rodent repellent and grinding aid is effective as a dusting agent where application of a powder is practicable. A two-component powder using a clay and rodent repellent, however, does not make an effective aqueous suspension, because the settling rate of the two components tends to make use of the material as a spraying agent impracticable. The mixture of rodent repellent and silica can be effectively used as a spray because the silica is a better suspending agent then clay when the powder formulations are mixed with water.

In a preferred embodiment of this invention, a multi-component mixture containing both a suspending agent, i.e. an agent which will aid in holding the other powdery constituents in an aqueous suspension, and a wetting agent, i.e. a compound that will aid in insuring that the aqueous dispersion will wet the variety of objects being treated and thus make the rodent repellent adhere to the objects, are added to the formulation.

Suspending agents that have been found suitable for use in thickening aqueous dispersions of the formulations of this invention and thereby preventing settling of the dispersed solids include hydroxalkyl cellulose compounds and bentonite and attapulgite clays and commerical formulations of suspension clays, such as Marasperse CB and Marasperse C-21, products of American Can Co. It has been found that the hydroxalkyl cellulose compounds are more practicable as suspending agents in the formulations of this invention and that one particularly preferred agent is a hydroxy-propyl methyl cellulose such as Methocel 65HG, a product of Dow Chemical Co. The suspending agent is added to the four-component mixture in an amount of about 2 to about 25 percent by weight of the total mixture, preferably in an amount of about 9.5 to about 10.5 percent by weight of the total mixture.

Commerical wetting agents generally available should be equally useful in the process of this invention. At present non-ionic wetting agents such as Triton X-100, a product of Rohm and Haas Corporation which is alkyl aryl polyether alcohol and Igepal CO-630, a product of GAP Corporation, nonylphenoxypoly(ethyleneoxy)ethanol are preferred. Of these the Igepal CO-630 is presently preferred because it currently has Environmental Protection Agency approval for use in formulations with commerically available rodent repellents of the type useful in this invention. The wetting agents can be used effectively in a range of about 0.1 to about 15 weight percent total of the four-component mixture, preferably in the range of about 9.5 to about 10.5 weight percent of the total mixture.

The formulations are prepared by adding either the two ingredients or the four ingredients of the mixtures to a ball mill and grinding them for about 15 minutes. Although a ball mill is preferred, other grinding apparatus can be used. A dry powder is obtained which can be applied as such to cables, pipes, or other objects which are to be protected against rodent attack. It has been found that grinding of the ingredients in excess of about 15 minutes tends to produce a mixture that fouls the grinding apparatus and also tends to be less effective as a free-flowing powder.

If it is preferred to apply a liquid dispersion of the formulation by spraying, the dry powder obtained as above is diluted with water with stirring at a ratio of about 24 gallons of water per pound of rodent repellent contained in the dry powder. Thus, if the dry powder contains 70 weight percent rodent repellent, the dilution ratio is 17.5 gallons of water per pound of dry powder. It has been found that 50 gallons of such a water dispersion is an effective rodent repellent when applied to one mile of an underground cable.

The following are specific examples showing the preparation of rodent repellent formulations according to the processes of this invention. These examples are meant to be illustrative and should not be taken as exclusive.

EXAMPLE 1

276 grams of N,N-dimethyl-S-tert butylsulfenyl dithiocarbamate and 24 grams of cab-o-sil, low-density silica, about 92 and 8 percent by weight respectively of the total composition were charged into a 1-gallon ball mill containing ⅜ inch milling balls. The mill was run for 10 minutes to produce a free-flowing powder. There was some trace of caking on the walls of the mill and more extensive caking on the milling balls.

EXAMPLE 2

285 grams of rodent repellent, N,N-dimethyl-S-tert butylsulfenyl dithiocarbamate and 15 grams of cab-o-sil, low-density silica, about 95 and 5 percent by weight of the total mixture respectively were charged into a 1-gallon ball mill containing ⅜ inch milling balls. The mill was operated for 15 minutes. After 10 minutes of operation both the walls and the milling balls were clean. After 15 minutes of operation the walls of the mill were essentially clean but there was caking on the milling balls.

The two examples above show the use of a milling or grinding aid with the rodent repellent to produce a dry powder. The two examples illustrate the effect of decreasing the relative amount of grinding aid on fouling the grinding apparatus. In both examples an acceptable free-flowing powder was produced, but as the grinding aid was decreased the tendency to foul the grinding apparatus increased.

In the following Table N,N-dimethyl-S-tert butylsulfenyl dithiocarbamate crystals and low-density silica were added to a 1-gallon ball mill containing ⅝ inch steel grinding balls along with suspending agent and wetting agent where noted. The ball mill was operated for time intervals as noted on the table, the condition of the grinding apparatus was noted and the powder produced was dispersed in tap water to give the equivalent of 2 pounds of rodent repellent in 50 gallons of water. The suspension was made with 150 grams of tap water in a stoppered test tube 30 millimeters ID by 29 millimeters long by shaking vigorously for 2 minutes. The test tube was then placed in an upright position and the amount of clear phase at the top and the settling at the bottom were measured several times in the period of 1 hour and the conditions of settling of the samples of the suspensions were noted. Table I below shows the composition of six different suspensions tested.

TABLE I

| Component | Sample A Grams | Sample A Conc., Wt. % | Sample B Grams | Sample B Conc., Wt. % | Sample C Grams | Sample C Conc., Wt. % | Sample D Grams | Sample D Conc., Wt. % | Sample E Grams | Sample E Conc., Wt. % | Sample F Grams | Sample F Conc., Wt. % |
|---|---|---|---|---|---|---|---|---|---|---|---|---|
| N,N-dimethyl-S-tert-butylsulfenyl dithiocarbamate | 10 | 67.0 | 220 | 78.6 | 220 | 75.9 | 220 | 78.4 | 220 | 74.4 | 220 | 70.9 |
| Igepal CO-630 | 1.4 | 9.4 | — | — | — | — | — | — | 30 | 10.1 | 30 | 9.7 |
| Xylene | 2.0 | 13.4 | — | — | — | — | — | — | — | — | — | — |
| Low Density Silica (Cab-O-Sil) | 1.5 | 10.2 | 30 | 10.7 | 40 | 13.8 | 40 | 14.2 | 40 | 13.5 | 30 | 9.7 |
| Triton X-100 | — | — | 30 | 10.7 | 30 | 10.3 | 15 | 5.3 | — | — | — | — |
| Methocel | — | — | — | — | — | — | 6 | 2.1 | 6 | 2.0 | 30 | 9.7 |
| Grinding time - hrs. | — | — | 2.5 | | 1.25 | | .25 | | .16 | | .16 | |
| TOTAL | 14.9 | 100.0 | 280 | 100.0 | 290 | 100.0 | 281 | 100.0 | 296 | 100.0 | 310 | 100.0 |

In noting the data in the Table above it can be seen that xylene can be used in the process of the invention as part of the grinding composition. The condition of the grinding apparatus after preparation of each of the samples in the Table above was as follows:

Sample A which was produced by grinding in a mortar the mixture of ingredients which had been heated together and stirred on a hot plate to produce a mixture resembling crumb rubber produced white, free-flowing powder without apparent fouling of the grinding apparatus;

Sample B was evidently deficient in silica as this formed a coating on both the walls of the grinding mill and the grinding balls and produced a sticky powder which, however, dispersed slowly, but completely, in water;

Sample C produced some caking on the mill walls and the milling balls but most of the product was a free-flowing powder which dispersed well in water, but settled out rapidly;

Sample D produced a free-flowing powder that dispersed well in water but tended to flocculate and settle fairly rapidly;

Sample E was produced by terminating the grinding operation when the powder began to stick to the milling surface and produced good dispersion in water which was a stable dispersion; and Sample F was produced without noting coating of the mill, dispersed well in water to form the best suspension tested.

It can be seen from the comments above that short milling times and relatively high ratios of suspending agent and wetting agent to the low-density inert solids produced the best overall characteristics of free-flowability of the product, good dispersion in water, and good retention of the suspension.

I claim:

1. A method for preparing a free-flowing, rodent repellent powder composition comprising grinding crystals of a rodent repellent effective N,N-dialkyl-sulfenyl dithiocarbamate selected from N,N-dimethyl-S-methylsulfenyl dithiocarbamate or N,N-dimethyl-S-tert butylsulfenyl dithiocarbamate with a grinding aid consisting essentially of low-density clay or low-density silica having a density of 5 pounds per cubic foot or less for a period of up to about 15 minutes, said period sufficient to produce a free-flowing powder.

2. A method according to claim 1 wherein the N,N-dialkyl-sulfenyl dithiocarbamate is N,N-dimethyl-S-tert butylsulfenyl dithiocarbamate.

3. A method of claim 1 wherein said grinding aid is added in an amount of about 11 to about 15 percent of the total composition.

4. A method according to claim 1 for preparing a free-flowing, rodent repellent, wettable powder composition wherein the grinding aid is a low-density silica added in an amount of about 11 to about 15 percent of the total composition.

5. A method according to claim 4 for preparing a free-flowing, rodent repellent, wettable powder composition wherein in addition to said grinding aid and rodent repellent an amount of a suspending agent inert to said N,N-dialkyl-sulfenyl dithiocarbamate in the range of about 2 to about 25 weight percent of the total mixture and a wetting agent in the amount of about 0.1 to about 15 percent by weight of the total mixture is also admixed into the composition.

6. A method according to claim 5 wherein the dithiocarbamate in N,N-dimethyl-S-tert butylsulfenyl dithiocarbamate and is about 10 to about 90 weight percent of the total composition, the grinding aid is about 5 to about 80 weight percent of the total composition, the suspending agent is about 2 to about 25 weight percent of the total composition and the wetting agent is about 0.1 to about 15 weight percent of the total composition.

7. A method according to claim 6 wherein the N,N-dimethyl-S-tert butylsulfenyl dithiocarbamate is about 68 to about 72 weight percent of the total composition, the grinding aid is about 9 to about 12 weight percent of the total composition, the suspending agent is about 9.5 to about 10.5 weight percent of the total composition and the wetting agent is about 9.5 to about 10.5 weight percent of the total composition.

8. A method according to claim 7 wherein the suspending agent is hydroxy-propyl methyl cellulose, and the wetting agent is nonyl phenoxypolyethyleneoxy ethanol.

9. A method for preparing a rodent repellent liquid suspension composition comprising the preparation of a rodent repellent powder by the method of claim 5 and admixing said composition with a sufficient amount of water to provide a rodent repellent effective suspension.

* * * * *

UNITED STATES PATENT AND TRADEMARK OFFICE
CERTIFICATE OF CORRECTION

PATENT NO. : 4,025,643

DATED : May 24, 1977

INVENTOR(S) : Paul F. Warner

It is certified that error appears in the above—identified patent and that said Letters Patent are hereby corrected as shown below:

Column 6, line 43, "in" should be --- is ---.

Signed and Sealed this

Twentieth Day of September 1977

[SEAL]

Attest:

RUTH C. MASON
Attesting Officer

LUTRELLE F. PARKER
Acting Commissioner of Patents and Trademarks